US 6,611,654 B1

(12) United States Patent
Shteyn

(10) Patent No.: US 6,611,654 B1
(45) Date of Patent: Aug. 26, 2003

(54) TIME- AND LOCATION-DRIVEN PERSONALIZED TV

(75) Inventor: Yevgeniy Eugene Shteyn, Cupertino, CA (US)

(73) Assignee: Koninklijke Philips Electronics NV, Eindhoven (NL)

( * ) Notice: Subject to any disclaimer, the term of this patent is extended or adjusted under 35 U.S.C. 154(b) by 0 days.

(21) Appl. No.: 09/283,545

(22) Filed: Apr. 1, 1999

(51) Int. Cl.[7] .............................. H04N 5/91; H04N 7/00; H04N 7/173
(52) U.S. Cl. ............................ 386/83; 386/46; 725/86
(58) Field of Search ............................ 386/69, 83, 46, 386/68, 1, 95, 4, 52, 55; 725/86, 87, 88, 101, 102, 103; H04N 5/91, 7/00, 7/173

(56) References Cited

U.S. PATENT DOCUMENTS 5,270,829 A * 12/1993 Yang
5,541,738 A * 7/1996 Mankovitz
5,589,945 A * 12/1996 Abecassis

FOREIGN PATENT DOCUMENTS

WO    WO 92/22983    * 12/1992
WO    WO 99/01984    * 1/1999

OTHER PUBLICATIONS

"Introducing the new face of television" at http://www.tivo.com/what/intro.html.
"Prime Time Anytime" at http://www.tivo.com/what/how.html.
"Frequently Asked Questions" at http://www.tivo.com/what/faq.html.
"Frequently Asked Questions" (details) at http://www.tivo.com/what/faq_sub.html#q02.

* cited by examiner

Primary Examiner—Robert Chevalier
(74) Attorney, Agent, or Firm—Gwenaelle Le Pennec

(57) ABSTRACT

A server system enables a subscriber to select a specific broadcast program for recording and a specific location and time frame for play-out of the recorded program.

7 Claims, 2 Drawing Sheets

TIME- AND LOCATION-DRIVEN PERSONALIZED TV

FIELD OF THE INVENTION

The invention relates to a system and method for providing information content to an end user.

BACKGROUND ART

Several companies, e.g., TiVo, Inc., have been developing recording devices that enable to time-shift (pause, rewind, and slow-motion) play-out of live TV broadcasts. The user has to subscribe to a service (provided via a modem), and to connect the device between a TV, and a satellite receiver, cable box or antenna. The service provides an electronic program guide (EPG) based on the user-profile that develops over time. The service learns from the user what he or she prefers and will automatically record favorite shows and make suggestions about other shows based on the user's preference profile.

OBJECT OF THE INVENTION

The inventor has realized that it is a disadvantage that the service is location-specific. That is, mobile users cannot chose desirable programming from, and for, multiple geographically different places along their itinerary. It is therefore an object of the invention to broaden the scope of the known systems and services to provide more degrees of freedom to the end user.

SUMMARY OF THE INVENTION

To this end, the invention provides a method of enabling a user to access content information (e.g., video, audio). The method enables the user to select the content information, e.g., from an electronic program guide relating to a broadcast or multicast service. The selected content information gets recorded when it is broadcasted or multicasted. The method enables the user to select in advance at least a specific one from multiple geographically different locations at which the recorded, selected content information will be made available for play-out. Preferably, the invention also enables the user to specify a time frame for making the recorded content information available for play-out at the specific location. The content information can be recorded at a first recording system, e.g., at a server, whereafter the recorded selected content information is streamed over a data network, e.g., over the Internet or a private network like AOL, from the first recording system to the location specified by the user. If the specific location has a second recording system, the streaming uses a low-bandwidth protocol so as to keep Internet bandwidth usage low while recording at the second recording system.

The invention lets the user specify in advance a location for play-out of a specific broadcast or multicast program pre-recorded in response to the user's selection, and has the content made available to him or her at that location. For example, the user can specify that he or she will be, e.g., at the house of a relative, at a specific hotel, on a particular flight of a specific airline, in a specific bar, a particular restaurant, etc., at a specific time period, and request that the content be recorded at this location. This requires that these other locations be integrated in the infrastructure of the service mentioned above.

The programs of a TV broadcasts are typically regional or local. If the user is traveling outside the region or the time zone, he or she may request to search for an identical program broadcasted in the new region, or a program of a similar content, or a program with identical or similar content but closer in time to the intended play-out, and record that program at a recording device in the pre-specified location.

Alternatively, or subsidiarily, a program can be recorded and stored temporarily at a server and then streamed over a data network, e.g., the Internet, using a low-bandwidth protocol, to a recording device specified by the user as destination. Note that bandwidth is not a critical factor in this service model or method of doing business, as recording and play-out occur as events separated in time.

The invention is based on an insight that several technological and demographic trends are emerging and gaining momentum: personalized information through Internet portals such as the web sites "my.yahoo.com", "my.excite.com", "cnn.com", etc. . . . ; personalized TV such as provided by TiVo, Inc.; the availability of EPG's; home networking and home automation infrastructures, e.g., HAVi, Home API, JINI., tailored to the individual's equipment, preferences and needs; teleconferencing; and an increasing mobility of the individual: business travel and recreational travel, and as a consequence thereof, an increasing demand for high quality services. Accordingly, the invention attempts to contribute to the user's needs by means of enabling shifting of recording and play-out locations, in addition to the time-shifting provided by the known services.

BRIEF DESCRIPTION OF THE DRAWINGS

The invention is explained by way of example and with reference to the accompanying drawings, wherein.

Throughout the figures, same reference numerals indicate similar or corresponding features.

PREFERRED EMBODIMENTS

Several scenarios are described below that illustrate attractive opportunities of exploiting the invention, with benefits to the end-user as well as to the service provider and content provider.

Figure 1:
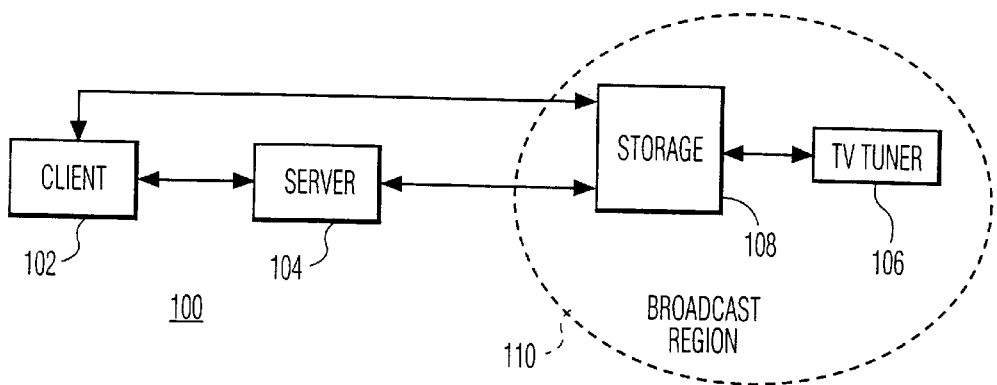
FIGS. 1–4 are block diagrams illustrating the method of the invention.
Figure 2:
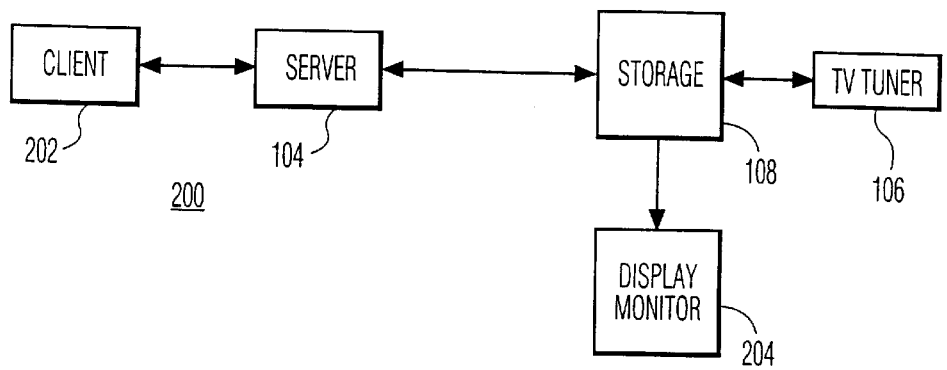

Travel services: Eugene is scheduled for an intercontinental business trip starting on a Sunday. An ice hockey game is broadcasted on Sunday by his local TV station at home. Eugene makes his reservations with a hotel that provides a program recording service. He specifies that he would like to watch the game in this hotel. FIG. 1 illustrates this process in a system 100 according to the invention. Client 102, here the hotel's system, forwards to a server system 104 a request to make available a recording of a certain broadcasted program. Server system 104 locates a tuner 106 and a storage system 108 within a region 110 wherein this particular program will be broadcasted. Upon having selected storage system 108, the latter is activated to record the program at the time of broadcast. Note that system 108 can be Eugene's own home recording system, as well as a storage system that belongs to a service provider in the particular region. During or upon recording, the recorded content is streamed over a data network, e.g., the Internet or over data networks as maintained by online services such as AOL or CompuServe, to hotel 102 using a low-bandwidth protocol. Hotel 102 records the content for scheduled play-out as desired by Eugene.

Assume that there are multiple broadcast regions available wherein the same program is scheduled for broadcasted within a certain time frame. Then, server system 104 preferably selects storage system 108 in that particular region 110 wherein the broadcast takes place at a time that is most convenient in view of the duration contemplated for storing the content at system 108 and at client 102 and in view of the time it takes to stream the content over the Internet. By minimizing the occupancy time at system 108 and at client 102, storage capacity usage is optimized towards being able to service a larger number end-users.

Preferably, confirmative communication protocols are used between client 102 and server 104 and between server 104 and storage system 108 in order to have confirmed that the various actions are being taken necessary to get the desired content to hotel 102 in time. For example, storage system 108 may be out of order or may have run out of memory space. In these cases, server 104 may activate another storage system or have the end-user notified of alternatives.

Similarly, flight reservations can be made together with a reservation for a personalized in-flight entertainment program tailored to the preferences of each passenger. Each passenger seat is provided with a play-out device for making available pre-recorded content, e.g., audio or video. Client 102, e.g., the airline operator, receives a request for a personalized entertainment program on a particular flight. The program is based on pre-recorded content as broadcasted by a specific TV channel. The operator forwards the request to server 104 that in turn finds appropriate region 110 with storage system 108. Upon or during recording a preselected program, the recorded content is supplied to client 102 for local recording and/or subsequent play-out during the flight. This could again be done via a low-bandwidth protocol, or via a dedicated interconnection that enables high-bandwidth downloading into client 102.

Figure 3:
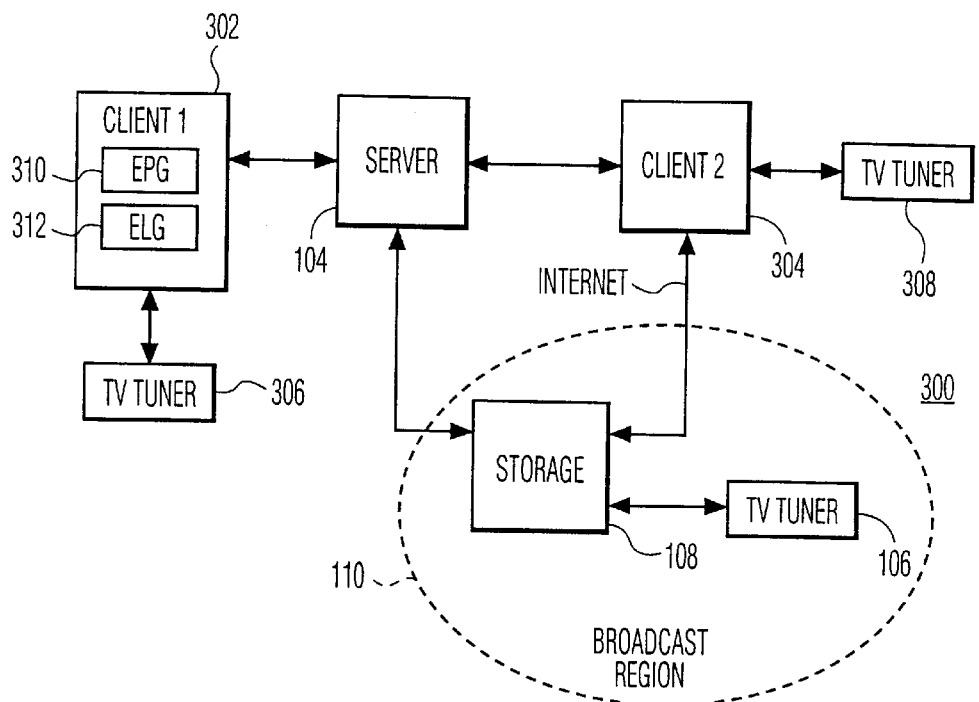

Ambient entertainment: Vladimir and his friends patronize a local sports bar establishment. They usually visit it on Fridays to relax after a long week at work. At the bar, they like to watch some basketball games together that were broadcasted in its entirety at the east coast earlier in the week. Vladimir and his friends, however, live on the west coast and saw only excerpts broadcasted by their local or regional TV station. FIG. 3 is a block diagram of a system 300 to illustrate how this can be achieved.

Vladimir and the sports bar proprietor have subscribed to a service provided by server 104. The service enables Vladimir and the proprietor to select broadcasts for being recorded at their own local client devices 302 and 304, respectively, and it enables Vladimir to record at the bar's client 304 with the authorization of the proprietor. Clients 302 and 304 are connected to local TV tuners 306 and 308, respectively, for recording local broadcasts. Each of clients 302 and 304 has a storage device (not shown), such as a hard disk, with a capacity large enough to store at least a few hours (play-out time) of video. Vladimir selects the desired program from an EPG 310 and the desired play-out location from an electronic location guide (ELG) 312. Both EPG 310 and ELG 312 are personalized services. In this case, the bar owner has authorized Vladimir to have bar's client 304 as a menu option in ELG 312. Vladimir therefore selects the broadcast of the basketball game for recording, and also the bar as location for play-out of the recorded basketball game. In addition, he specifies that he wants to have it available at the bar on Friday night later that week. Upon receiving this information from client 304, server 104 selects the appropriate region, here region 110, for locally recording the broadcast on storage system 108. After recording, the recorded content is supplied to client 304, e.g., via the Internet using a low-bandwidth protocol for local recording. Alternatively, if the desired broadcast takes place within the same region as that containing client 304, the recording of the content during the broadcast is made at client 304 directly without server storage 108 but under control of the server 104. In yet another scenario, server storage 108 is involved even if the broadcast takes place in the same region as wherein client 304 is located, for example, in order to relieve the local storage of client 304 that is typically more limited than that of server storage 108. Client 304 notifies server 104 of storage space available locally or already reserved for local recording, so that server storage 108 can serve as a temporary buffer. In yet another scenario, if there is sufficient bandwidth available, server storage 108 may stream the content directly to client 304 for play-out, i.e., without local pre-recording at client 304.

Figure 4:
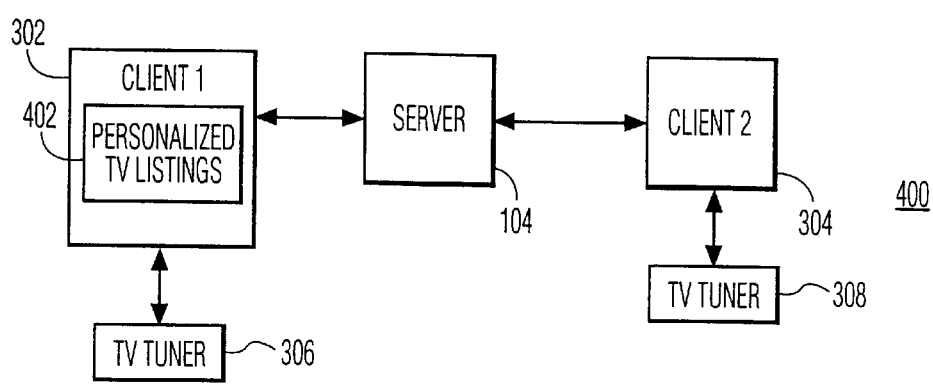

Web-based programming: FIG. 4 illustrates another scenario in a system 400. Svetlana accesses her personalized web page with TV listings 402 on her client 302. TV listings 402 are provided by services such as personalized information sites through Internet portals. She spots her favorite show, and decides to watch it later tonight. Svetlana remembers, however, that she has promised to visit her parents this evening. Instead of setting up the recording at her own client 402, she chooses to record the show on system 304 of her parents, so they can watch it together. She is authorized to make the reservation through server 108.

Examples of other scenarios illustrating the invention: Mobile user: Alice got stuck in traffic on her way home. She is going to be late for the broadcast of a live piano concert. Fortunately, her palm-top Nino (or cell phone, or laptop) can access the TV programming network. With just a couple of clicks Alice sets her recording time-shifting device to cache the concert. Enhanced Teleconference: Alice loves talking about her favorite TV series. She watches the episodes frequently and enjoys every minute of it. In today's episode one of the characters behaves exactly as she predicted a couple of days ago. Alice needs to talk to her friend Jane about it. Jane is at work and cannot see the show. Alice brings up her net menu and is authorized to select Jane's recording device. It has enough space reserved just for Alice. One click and today's phone discussion (telecon) with Jane is going to be a real time experience. of See within this context also: U.S. Ser. No. 09/053,448 filed Apr. 1, 1998 for Raoul Mallart and Atul Sinha for GROUP-WISE VIDEO CONFERENCING USES 3D-GRAPHICS MODEL OF BROADCAST EVENT; U.S. Ser. No. 09/138,782 filed Aug. 24, 1998 for Raoul Mallart and Atul Sinha for EMULATION OF STREAMING OVER THE INTERNET IN A BROADCAST APPLICATION; U.S. Ser. No. 09/149,950 filed Sep. 9, 1998 for Raoul Mallart for REAL TIME VIDEO GAME USES EMULATION OF STREAMING OVER THE INTERNET IN A BROADCAST EVENT; all incorporated herein by reference.

Above scenario's can be further enhanced by, e.g., having server 104 searching for a program identical to the one desired by the end-user but being broadcasted closer in time to the desired play-out time. This enables to reduce storage time at server storage 108. Alternatively, if the desired content is not available, the server may request the end-user to search for a program not-identical but of a similar type (e.g., western, football match, concert).

I claim:

1. A method of enabling a user to access content, the method comprising:

identifying by a user a device to which a plurality of contents will be broadcasted and the device having an associated user interface for locally controlling the device;

selecting by the user a future broadcasted content from the plurality of contents;

setting up the device to record the content when the content is broadcasted to the device; and wherein
the selecting and the identifying are done over the Internet via a web site different from the local user interface.

2. A method of enabling a user to access content, the method comprising:

providing user access to a server via a web site on the Internet;

enabling identifying on the web site a device of the user to which a plurality of contents will be broadcasted;

selecting by the user a future broadcasted content from the plurality of contents;

setting up the device by the server through a connection from the server to the device to record the future broadcasted content.

3. A system comprising:

a server on the Internet accessible to a user via a web site;

a device accessible by the server;

wherein,
the server is configured to receive input from the user via the web site, the input including a selection of a content from a plurality of contents that will be broadcasted to the device and a request to record the content and in response to the input, the server is configured to set up the device to record a future broadcast of the content.

4. The system of claim 3, wherein the device is accessible by the server over the Internet.

5. The system of claim 3, wherein the device is accessible by the server over a phone line.

6. The system of claim 3, wherein the selection of the content from the plurality of contents is done from an electronic program guide on the web site.

7. The system of claim 3, wherein the web site is accessible to the user from a personal digital assistant of the user.

* * * * *

(12) EX PARTE REEXAMINATION CERTIFICATE (8681st)
United States Patent
Shteyn

(10) Number: US 6,611,654 C1
(45) Certificate Issued: Nov. 22, 2011

(54) TIME- AND LOCATION-DRIVEN PERSONALIZED TV

(75) Inventor: Yevgeniy Eugene Shteyn, Cupertino, CA (US)

(73) Assignee: Philipe Electronics North America Corporation, New York, NY (US)

Reexamination Request:
No. 90/011,048, Jul. 30, 2010

Reexamination Certificate for:
Patent No.: 6,611,654
Issued: Aug. 26, 2003
Appl. No.: 09/283,545
Filed: Apr. 1, 1999

(51) Int. Cl.
*H04L 12/28* (2006.01)
*H04N 5/76* (2006.01)

(52) U.S. Cl. .......... 386/291; 386/296; 386/297; 386/298; 386/299; 386/E5.001; 725/86

(58) Field of Classification Search ............... None
See application file for complete search history.

(56) References Cited

To view the complete listing of prior art documents cited during the proceeding for Reexamination Control Number 90/011,048, please refer to the USPTO's public Patent Application Information Retrieval (PAIR) system under the Display References tab.

*Primary Examiner* — Ovidio Escalante

(57) ABSTRACT

A server system enables a subscriber to select a specific broadcast program for recording and a specific location and time frame for play-out of the recorded program.

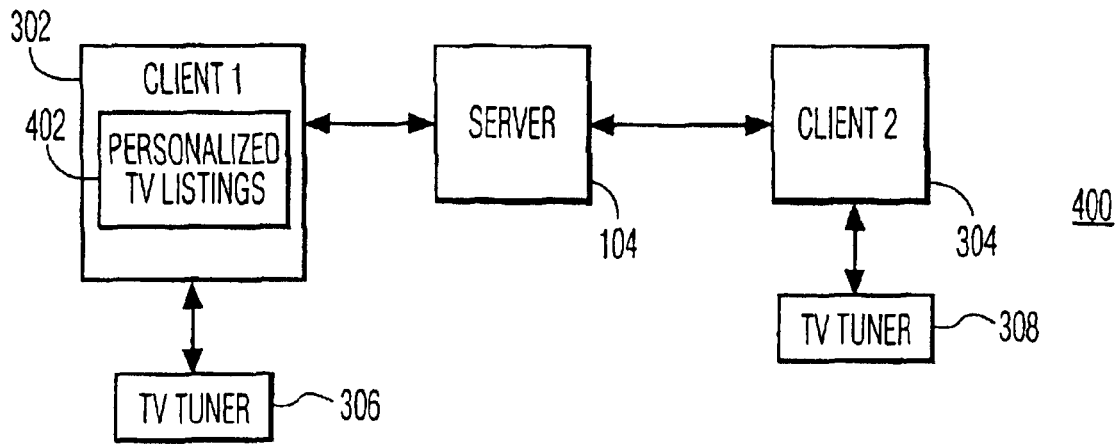

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3 are determined to be patentable as amended.

Claims 4-7, dependent on an amended claim, are determined to be patentable.

New claims 8-13 are added and determined to be patentable.

1. A method of enabling a user to access content, the method comprising *acts of*:
   identifying by a user *from a plurality of devices connected to the Internet each at geographically different broadcast regions* a device to which a plurality of contents will be broadcasted[and], the device having an associated user interface for locally controlling the device;
   selecting by the user a [future broadcasted] content from the plurality of contents *scheduled for broadcast*; *and*
   setting up the device to record the content when the content is broadcasted to the device[; and],
   wherein the selecting and the identifying are done over the Internet via a web site *having an associated remote user interface* different from the local user interface.

2. A method of enabling a user to access content, the method comprising:
   providing user access to a server via a web site on the Internet;
   enabling identifying on the web site *from a plurality of devices connected to the Internet each at geographically different broadcast regions* a device of the user to which a plurality of contents will be broadcasted;
   selecting by the user a [future broadcasted] content from the plurality of contents *scheduled for broadcast*; *and*
   setting up the device by the server through a connection from the server to the device to record *when* the [future broadcasted] content *is broadcasted*.

3. A system comprising:
   a server on the Internet accessible to a user via a web site; and
   a device *of a plurality of devices connected to the Internet each at geographically different broadcast regions, each* accessible by the server;
   wherein[,] the server is configured to receive input from the user [via] *on* the web site, the input including a selection of a content from a plurality of contents that [will] *are scheduled to* be broadcasted to the device and a request to record the content and in response to the input, the server is configured to set up the device to record *when* a [future] broadcast of the content *is enabled*.

8. *A method of enabling a user to access content, the method comprising acts of:*
   *identifying, by a user, a region having one or more of a plurality of devices to which one or more content will be broadcasted and the plurality of devices each having an associated user interface for locally controlling the device;*
   *selecting by the user a future broadcasted content from the plurality of contents;*
   *setting up one or more of said devices in the indentified region to record the content, with the setting up occurring prior to the content being broadcasted to the region; and*
   *providing the recorded content to one or more of said devices within said region,*
   *wherein the selecting and the identifying are done over the interest via a web site different from the local user interface.*

9. *The method of claim 1, wherein the setting up act includes programming the device to record the content when the content is broadcasted.*

10. *The method of claim 1, wherein the selecting act uses an electronic program guide and the identifying act uses an electronic location guide.*

11. *A system comprising:*
    *a server on the Internet accessible to a cell phone via a web site;*
    *a plurality of devices connected to the Internet each at geographically different broadcast regions, each accessible by the server;*
    *wherein the server is configured*
    *to receive input via the web site from the cell phone using a local user interface, the input including an identification of one or more of said plurality of devices and a selection of a content from a plurality of contents that are scheduled to be broadcasted to the one or more devices, and a request to record the content, and*
    *in response to the input, the server is configured to set up the one or more devices to record the content with the server setting up the one or more devices prior to the broadcast of the content.*

12. *A system comprising:*
    *a server on the Internet accessible to a laptop via the web site;*
    *a device of a plurality of devices connected to the Internet each at geographically different broadcast regions, each accessible by the server;*
    *wherein the server is configured to receive input via the web site from the laptop using a local user interface, the input including a selection of a content from a plurality of contents that are scheduled to be broadcasted to the device, and a request to record the content and in response to the input, the server is configured to set up the device to record the content with the server setting up the device prior to the broadcast of the content.*

13. *The system of claim 3, wherein the device is one of a plurality of devices accessible by the server, the input including identification of one or more of said devices, and the server is configured to set up the one or more identified devices to record the content prior to the broadcast of the content.*

\* \* \* \* \*